United States Patent
Clarke et al.

(10) Patent No.: US 8,440,224 B2
(45) Date of Patent: *May 14, 2013

(54) MULTI-COMPONENT PHARMACEUTICAL DOSAGE FORM

(75) Inventors: Allan J Clarke, King of Prussia, PA (US); Teodoro Fonio, Arese (IT); Geoffrey Arthur Harris, Worthing (GB); Ron Kift, Harlow (GB); Donald Lightfoot, Collegeville, PA (US); Shane McGinley, Collegeville, PA (US); Thomas Ofsharick, Collegeville, PA (US); Margaret Mary Szymczak, Philadelphia, PA (US)

(73) Assignee: Capsugel Belgium NV, Bornem (BE)

( * ) Notice: Subject to any disclaimer, the term of this patent is extended or adjusted under 35 U.S.C. 154(b) by 330 days.

This patent is subject to a terminal disclaimer.

(21) Appl. No.: 12/689,015

(22) Filed: Jan. 18, 2010

(65) Prior Publication Data
US 2010/0119597 A1 May 13, 2010

Related U.S. Application Data

(63) Continuation of application No. 11/611,281, filed on Dec. 15, 2006, now Pat. No. 7,691,407, which is a continuation of application No. 10/049,227, filed as application No. PCT/EP00/07295 on Jul. 27, 2000, now Pat. No. 7,163,693.

(30) Foreign Application Priority Data

| Jul. 30, 1999 | (GB) | 9917772.7 |
| Jul. 30, 1999 | (GB) | 9917774.3 |
| Jul. 30, 1999 | (GB) | 9917775.0 |
| Jul. 30, 1999 | (GB) | 9917777.6 |

(51) Int. Cl.
*A61K 9/48* (2006.01)

(52) U.S. Cl.
USPC .......................... 424/453; 424/451; 424/454

(58) Field of Classification Search .................. None
See application file for complete search history.

(56) References Cited

U.S. PATENT DOCUMENTS

| 3,186,910 A | 6/1965 | Glassman |
| 3,228,789 A | 1/1966 | Glassman |

(Continued)

FOREIGN PATENT DOCUMENTS

| BE | 900950 | 4/1985 |
| CA | 2188185 C | 10/1995 |

(Continued)

OTHER PUBLICATIONS

Cuff et al., Pharmaceutical Technology, Jun. 1998 pp. 96-106.

(Continued)

*Primary Examiner* — Susan Tran
(74) *Attorney, Agent, or Firm* — Finnegan, Henderson, Farabow, Garrett & Dunner, LLP

(57) ABSTRACT

A multi-component pharmaceutical dosage form comprising a plurality of drug substance—containing sub-units, being capsule compartments and/or solid sub-units comprising a solid matrix of a polymer which contains a drug substance, the sub-units being connected together in the assembled dosage form by a weld between parts of the assembled dosage form.

14 Claims, 5 Drawing Sheets

U.S. PATENT DOCUMENTS

Figure 1:
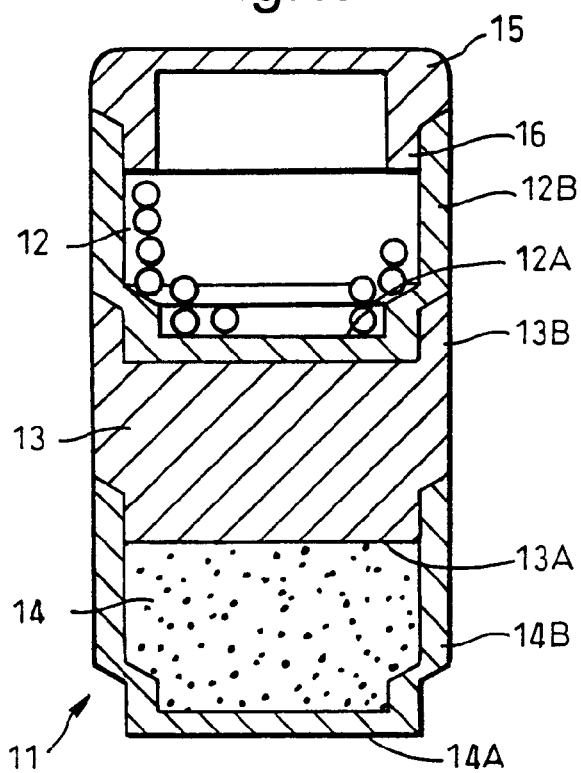

| | | | |
|---|---|---|---|
| 3,399,803 A | 9/1968 | Oglevee et al. | |
| 3,508,678 A | 4/1970 | Graham et al. | |
| 4,196,565 A | 4/1980 | Bodenmann et al. | |
| 4,250,097 A | 2/1981 | Pfister | |
| 4,281,763 A | 8/1981 | Pace | |
| 4,417,591 A | 11/1983 | Culver | |
| 4,487,327 A | 12/1984 | Grayson | |
| 4,498,080 A | 2/1985 | Culver | |
| 4,543,138 A | 9/1985 | Bollinger et al. | |
| 4,550,238 A | 10/1985 | Van Herle et al. | |
| 4,557,180 A | 12/1985 | Glomeau | |
| 4,564,363 A | 1/1986 | Bagnall et al. | |
| 4,576,284 A | 3/1986 | Wittwer | |
| 4,591,475 A | 5/1986 | Tomka et al. | |
| D285,837 S | 9/1986 | Wittwer | |
| 4,625,513 A | 12/1986 | Glomeau | |
| 4,655,840 A | 4/1987 | Wittwer et al. | |
| 4,663,148 A | 5/1987 | Eckenhoff et al. | |
| 4,673,438 A | 6/1987 | Wittwer et al. | |
| 4,678,516 A | 7/1987 | Alderman et al. | |
| 4,696,163 A | 9/1987 | Glomeau | |
| 4,724,019 A | 2/1988 | Brown et al. | |
| 4,738,724 A | 4/1988 | Wittwer et al. | |
| 4,738,817 A | 4/1988 | Wittwer et al. | |
| 4,764,378 A | 8/1988 | Keith et al. | |
| 4,766,728 A | 8/1988 | Glomeau | |
| 4,790,881 A | 12/1988 | Wittwer et al. | |
| 4,792,451 A | 12/1988 | Kim | |
| 4,793,493 A | 12/1988 | Makiej | |
| 4,806,337 A | 2/1989 | Snipes et al. | |
| 4,899,516 A | 2/1990 | Krieger et al. | |
| 4,928,840 A | 5/1990 | Barshay et al. | |
| 4,936,461 A | 6/1990 | Makiej et al. | |
| 4,964,262 A | 10/1990 | Moser et al. | |
| 5,004,601 A | 4/1991 | Snipes | |
| 5,047,248 A * | 9/1991 | Calanchi et al. | 424/485 |
| 5,074,426 A * | 12/1991 | Goodhart et al. | 220/4.24 |
| 5,082,655 A | 1/1992 | Snipes et al. | |
| 5,085,033 A | 2/1992 | Graham | |
| 5,135,752 A | 8/1992 | Snipes | |
| 5,139,790 A | 8/1992 | Snipes | |
| 5,236,689 A | 8/1993 | Wong et al. | |
| RE34,390 E | 9/1993 | Culver | |
| 5,244,668 A | 9/1993 | Snipes | |
| 5,312,008 A | 5/1994 | Davis | |
| 5,312,388 A * | 5/1994 | Wong et al. | 604/892.1 |
| 5,387,421 A | 2/1995 | Amidon et al. | |
| 5,443,461 A | 8/1995 | Atkinson et al. | |
| 5,456,919 A | 10/1995 | Patell et al. | |
| 5,672,359 A | 9/1997 | Digenis et al. | |
| 5,674,530 A | 10/1997 | Crison et al. | |
| 5,705,189 A | 1/1998 | Lehmann et al. | |
| 5,709,881 A * | 1/1998 | de Haan et al. | 424/465 |
| 5,750,143 A | 5/1998 | Rashid et al. | |
| 5,769,267 A | 6/1998 | Duynslager et al. | |
| 5,770,224 A | 6/1998 | Rashid et al. | |
| 5,976,571 A | 11/1999 | Crison et al. | |
| 6,153,218 A | 11/2000 | Barnwell et al. | |
| 6,200,600 B1 | 3/2001 | Rashid | |
| 6,207,191 B1 * | 3/2001 | Crison et al. | 424/472 |
| 6,248,807 B1 | 6/2001 | Sosa et al. | |
| 6,290,990 B1 | 9/2001 | Grabowski et al. | |
| 6,322,816 B1 | 11/2001 | Zeidler et al. | |
| 6,367,228 B1 | 4/2002 | Wurst et al. | |
| 6,387,401 B2 | 5/2002 | Rosenberg et al. | |
| 6,489,378 B1 | 12/2002 | Sosa et al. | |
| 6,528,089 B1 | 3/2003 | Kothrade et al. | |
| 6,613,353 B1 | 9/2003 | Barnwell et al. | |
| D481,456 S | 10/2003 | McAllister et al. | |
| D493,518 S | 7/2004 | McAllister et al. | |
| D501,549 S | 2/2005 | McAllister et al. | |
| D501,550 S | 2/2005 | McAllister et al. | |
| D506,545 S | 6/2005 | McAllister et al. | |
| D516,714 S | 3/2006 | McAllister et al. | |
| 7,022,344 B1 | 4/2006 | Kothrade et al. | |
| 2001/0007664 A1 | 7/2001 | Rosenberg et al. | |
| 2001/0008637 A1 | 7/2001 | Hochrainer et al. | |
| 2003/0008973 A1 | 1/2003 | Sosa et al. | |
| 2003/0029558 A1 | 2/2003 | Hochrainer et al. | |
| 2003/0049311 A1 | 3/2003 | McAllister et al. | |
| 2003/0068369 A1 | 4/2003 | McAllister et al. | |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2003/0194431 A1 | 10/2003 | Miller et al. | |
| 2004/0115256 A1 | 6/2004 | McAllister et al. | |
| 2004/0131668 A1 | 7/2004 | Hochrainer et al. | |
| 2004/0166153 A1 | 8/2004 | McAllister et al. | |
| 2005/0008690 A1 | 1/2005 | Miller | |
| 2005/0129757 A1 | 6/2005 | Kothrade et al. | |
| 2005/0175687 A1 | 8/2005 | McAllister et al. | |
| 2005/0191347 A1 | 9/2005 | Barnwell et al. | |
| 2005/0249807 A1 | 11/2005 | Brown et al. | |
| 2006/0057201 A1 | 3/2006 | Bonney et al. | |
| 2006/0177496 A1 | 8/2006 | McAllister et al. | |

FOREIGN PATENT DOCUMENTS

| | | |
|---|---|---|
| CA | 2227272 A1 | 3/1997 |
| CA | 2298659 A1 | 2/1999 |
| CA | 2311308 A1 | 6/1999 |
| CA | 2264287 A1 | 9/1999 |
| DE | 3524963 | 1/1987 |
| DE | 3543912 | 6/1987 |
| DE | 3727894 | 3/1989 |
| EP | 141397 | 10/1984 |
| EP | 0211079 | 1/1985 |
| EP | 143524 | 6/1985 |
| EP | 0228067 | 12/1986 |
| EP | 0274345 A1 | 7/1988 |
| EP | 384642 A1 | 8/1990 |
| FR | 1454013 | 7/1966 |
| FR | 2524311 | 10/1983 |
| GB | 1108629 | 4/1968 |
| GB | 1177587 | 1/1970 |
| GB | 1496737 | 6/1975 |
| GB | 2172569 | 3/1985 |
| GB | 2148235 A | 5/1985 |
| GB | 2148841 A | 6/1985 |
| GB | 2187703 | 9/1987 |
| JP | 50-140996 | 11/1975 |
| JP | 54-59312 | 5/1979 |
| JP | 58-501157 | 7/1983 |
| JP | 63-135174 | 6/1988 |
| NL | 7610038 | 3/1978 |
| WO | WO 83/00477 | 2/1983 |
| WO | WO 90/11070 | 10/1990 |
| WO | WO 90/12567 | 11/1990 |
| WO | WO 92/13521 | 8/1992 |
| WO | WO 94/09743 | 5/1994 |
| WO | WO 95/13056 | 5/1995 |
| WO | WO 95/16438 | 6/1995 |
| WO | WO 01/39751 | 6/2001 |
| WO | WO 01/43935 | 6/2001 |
| WO | WO 02/060384 A2 | 8/2002 |
| WO | WO 02/060385 A2 | 8/2002 |
| WO | WO 03/043601 | 5/2003 |
| WO | WO 03/086267 A2 | 10/2003 |
| WO | WO 2004/010978 | 2/2004 |
| WO | WO 2005/009380 A2 | 2/2005 |
| WO | WO 2005/089726 A1 | 9/2005 |

OTHER PUBLICATIONS

English translation of BE 900950 Abstract.
English translation of FR 1454013 Abstract.
English translation of JP 54-59312 claim 1.
English translation of JP 50-140996 claim 1.
English translation of DE 3524963 Abstract, 1987.
English translation of DE 3543912 Abstract, 1987.
English translation of DE 3727894 Abstract, 1989.
English translation of FR 2524311 Abstract, 1983.
English translation of NL 7610038 Abstract, 1978.

* cited by examiner

MULTI-COMPONENT PHARMACEUTICAL DOSAGE FORM

This application is a continuation of U.S. application Ser. No. 11/611,281 filed 15 Dec. 2006 now U.S. Pat. No.7,691,407 (allowed) which is a continuation of U.S. application Ser. No. 10/049,227 filed 23 Sep. 2002 now patent 7,163,693, which is a National Stage Application filed under 35U.S.C.§371 of PCT/EP00/07295 filed 27 Jul. 2000.

This invention relates to pharmaceutical formulations, being a dosage form comprising two or more connected sub-units, particularly for oral dosing.

Various types of pharmaceutical dosage form are known for oral dosing. Pharmaceutical capsules are well known, generally being intended for oral dosing. Such capsules generally comprise an envelope wall of a pharmaceutically acceptable, e.g. orally ingestible, polymer material such as gelatin, although other materials for capsule walls, e.g. starch and cellulose based polymers are also known. Such capsules generally have soft walls made by making a film on a capsule former, which is then allowed to dry. Rigid walled capsules made by injection moulding are also known, see for example U.S. Pat. Nos. 4,576,284, 4,591,475, 4,655,840, 4,738,724, 4,738,817 and 4,790,881 (all to Warner Lambert). These disclose specific constructions of capsules made of gelatin, starch and other polymers, and methods of making them by injection moulding of hydrophilic polymer—water mixtures. U.S. Pat. No. 4,576,284 specifically discloses such capsules provided with a cap which closes the capsule, and which is formed in situ on the filled capsule by moulding. U.S. Pat. No. 4,738,724 discloses a wide range of rigid capsule shapes and parts.

Multi-compartment capsules, including those of the type where each compartment has different drug release characteristics or for example contains a different drug substance or formulation are also known, for example in U.S. Pat. No. 4,738,724 (Warner-Lambert), U.S. Pat. No. 5,672,359 (University of Kentucky), U.S. Pat. No. 5,443,461 (Alza Corp.), WO 9516438 (Cortecs Ltd.), WO 9012567 (Helminthology Inst.), DE-A-3727894, BE 900950 (Warner Lambert), FR 2524311, NL 7610038 (Tapanhony NV), FR 28646 (Pluripharm), U.S. Pat. No. 3,228,789 (Glassman), U.S. Pat. No. 3,186,910 (Glassman) among others. U.S. Pat. No. 4,738,817 discloses a multicompartment capsule with a similar construction to those of U.S. Pat. No. 3,228,789 and U.S. Pat. No. 3,186,910, made of a water-plasticised gelatin.

Pharmaceutical dosage forms are also known which comprise a matrix of a solid polymer, in which a drug substance is dispersed, embedded or dissolved as a solid solution. Such matrixes may be formed by an injection moulding process. This technology is discussed in Cuff G, and Raouf F, Pharmaceutical Technology Jun. 1998 p 96-106. Some specific formulations for such dosage forms are for example disclosed in U.S. Pat. Nos. 4,678,516; 4,806,337; 4,764,3785,004,601; 5,135,752; 5,244,668; 5,139,790; 5,082,655 among others; in which a polyethylene glycol ("PEG") matrix is used and solid dosage forms are made by injection moulding.

The content of the above-mentioned background publications is incorporated herein by way of reference.

It is an object of this invention to provide an alternative and improved pharmaceutical dosage form which provides inter alia greater flexibility in producing a dosage form adapted to a patient's specific administration requirement, and to ease of manufacture. Other objects and advantages of the invention will be apparent from the following description.

According to this invention a multi-component dosage form is provided which comprises a plurality of drug substance—containing sub-units each selected from capsule compartments which can release their drug substance in the gastro-intestinal environment, and solid sub-units comprising a solid matrix of a polymer which contains a drug substance, the polymer being soluble, dispersible or disintegrable in the patient's gastro-intestinal environment to thereby release the drug substance, the sub-units being connected together in the assembled dosage form and being retained together by the connection at least prior to administration to a patient, wherein the connection is provided by a weld between parts of the assembled dosage form.

The connectable nature of these sub-units advantageously enables various sub-units having different drug release characteristics and/or contents to be assembled and connected together to produce a dosage form. In a preferred form the sub-units have common interchangeable interconnectable parts so that the sub-units of the invention may be assembled in various combinations using the same basic units of capsule compartments, solid sub-units, or of solid sub-units and capsule compartments. This can facilitate the rapid prototyping of a dosage form comprising a combination of different drug substances in respective sub-units, and/or combinations of the same or different drug substances with different release characteristics, whilst simplifying the formulation procedure.

In a first embodiment of this invention the pharmaceutical dosage form comprises a plurality of capsule compartments each bounded and physically separated from at least one adjacent compartment by a wall made of a pharmaceutically acceptable polymer material, adjacent compartments being connected together in the assembled dosage form and being retained together by the connection at least prior to administration to a patient, one or more of the compartments containing a drug substance, and wherein the connection is provided by a weld between parts of the assembled dosage form, suitably between immediately adjacent parts.

Suitably in the assembled dosage form of this first embodiment there are at least two, for example three, such capsule compartments. Three or more such compartments may be linearly disposed in the assembled dosage form, e.g. in an arrangement comprising two end compartments at opposite ends of the line, and one or more intermediate compartments. Suitably there may be two such capsule compartments.

In a second embodiment of this invention the pharmaceutical dosage form comprises a plurality of drug-containing sub-units connected together in the assembled dosage form and being retained together by the connection at least prior to administration to a patient, at least one of the sub-units being a solid sub-unit comprising a solid matrix of a polymer which contains a drug substance, the polymer being soluble, dispersible or disintegrable in the patient's gastro-intestinal environment to thereby release the drug substance, and wherein the connection is provided by a weld between parts of the assembled dosage form.

In one form of this second embodiment all of the sub-units in the dosage form of this invention may be solid sub-units, e.g. two or more such solid sub-units, e.g. three such solid sub-units.

In another form of this second embodiment, one or more of the sub-units comprise a solid sub-unit, and one or more of the other sub-units may comprises a capsule compartment bounded by a wall made of a pharmaceutically acceptable polymer material, one or more of the said capsule compartments containing a drug substance.

Suitably in the assembled dosage form there are at least two, for example three or more, e.g. four sub units. Such an assembled dosage form may comprise three or four sub-units comprising one, two or three solid sub-units, combined with independently one, two or three capsule sub-units. Three or more such sub-units may for example be linearly disposed in the assembled dosage form, e.g. in an arrangement comprising two end sub-units at opposite ends of the line, and one or more intermediate sub-units. For example such an assembled dosage form may comprise a solid sub-unit connected to a capsule compartment; a solid sub-unit between two end capsule compartments; an end capsule compartment, an intermediate capsule compartment and an end solid sub-unit; an end capsule compartment, an intermediate solid sub-unit and an end solid sub-unit; or an intermediate capsule compartment between two end solid sub-units. An assembled dosage of four such sub-units may comprise two end solid sub-units, an intermediate solid sub-unit and an intermediate capsule compartment. Alternately it may comprise two end solid sub-units with two intermediate capsule sub-units, or other combinations of sub-units.

In one embodiment one or more, e.g. all, of the sub-units may for example be substantially cylindrical, which term includes shapes which have a circular, oval or oblate circular cross section across the longitudinal axis, and shapes which have parallel or tapering e.g. with side walls which taper conically over at least part of their extent. Solid sub-units may also be substantially cylindrical in shape. Such substantially cylindrical sub-units may be provided with connectable parts at one or both of their longitudinally disposed ends so that the assembled dosage form may also be overall of a substantially cylindrical shape.

A preferred form of the multi-component dosage form of this invention comprises two capsule compartments.

The invention also provides individual sub-units, e.g. individual capsule compartments or solid sub-units adapted for use in the assembled dosage form.

In the assembled dosage form the adjacent sub-units, whether capsule compartments, solid sub-units or combinations thereof, are connected together by means of a weld at the area where two adjacent parts of the dosage form, e.g. sub-units, are in contact, e.g. a thermal weld, an ultrasonic or inductive weld, or an adhesive weld (e.g. curable adhesives such as UV curable adhesive). A thermal weld may for example be achieved by bringing sub-units into adjacent contact and applying localised heating for example produced by directing a laser beam or a fine jet of hot gas e.g. nitrogen at the area where two adjacent sub-units are in contact. In thermal, inductive and ultrasonic welding normally localised fusion together of the materials of adjacent parts of the dosage form which are in contact occurs, and on subsequent solidification of the materials a bond is formed between the adjacent parts. An adhesive weld may be achieved by applying an adhesive (e.g. curable adhesives such as UV curable adhesive) to parts of the dosage form which when the dosage form is assembled are in contact, and then causing or allowing the adhesive to set.

The multi-component dosage form of the present invention is particularly suited to fabrication using ultrasonic welding.

Ultrasonic welding is a known technique involving the use of high frequency sound energy to soften or melt a thermoplastic material at the site where a joint with the material is required. A general description of ultrasonic welding is for example to be found in the publication "Ultrasonic Welding of Thermoplastics" (TWI Ltd., Abington, Cambridgeshire GB, (1997)). Parts to be joined are held together under pressure and then subjected to ultrasonic vibrations usually at a frequency of 20-40 kHz. The actual mechanism responsible for the generation of heat at the joint site is not well understood. An ultrasonic welding machine comprises five main components, being a power supply, a control system, a welding head, fixturing to hold the parts to be welded, and a system to apply the required pressure. The power supply converts electricity into high frequency electric power which drives a transducer, e.g. a piezoelectric transducer, which converts electrical energy, e.g. from the mains supply, into mechanical, i.e. ultrasonic, energy. Between the transducer and the parts to be welded is located a booster and horn system, being a usually metallic component which serves to amplify the ultrasonic waves (the booster horn), transmit the clamping pressure, and deliver the sound energy to the part to be welded (the sonotrode or welding horn). For successful ultrasonic welding careful design of the parts to be welded and set up of the welding equipment is important.

Adjacent parts of the dosage form of the invention, e.g. of adjacent sub-units may have features to facilitate the connection of the parts together, particularly to assist or supplement the weld.

For example adjacent parts, e.g. sub-units, of the dosage form of this invention may have substantially planar regions of their surface which may be brought into contact and then the weld may be formed, or may have regions of their surface of complementary, preferably interconnecting shapes, thereby facilitating connecting sub-units together by engagement of these complementary shaped parts.

Preferably, additionally or alternatively adjacent sub-units may be provided with respectively inter-connectable first and second connectable parts such that the first connectable part on one sub-unit may connect with the second connectable part on an adjacent part of the dosage form, e.g. an adjacent sub-unit in a suitable configuration, e.g. in the above-mentioned linear configuration. This interconnection may contribute to the strength of bond achieved by the weld, or additionally or alternatively may help to hold adjacent parts of the dosage form together prior to and in readiness for the weld to be formed and contributes to the retention of the adjacent sub-units together, e.g. via a retaining friction, snap, screw or other kind of fit between the connectable parts. The connectable parts may be such as to facilitate the assembly together of the sub-units in preferred configurations, e.g. the connectable part(s) on one or more one sub-unit may be such as to only connect with a corresponding connectable part on other selected sub-units but not with non-corresponding connectable parts on other sub-units. Alternatively the connectable parts on the sub-units may be common and interchangeable so that the sub-units may be connected together in a wide range of combinations. This means inter alia that otherwise different capsule compartments or solid sub-units may have mutually connectable parts so that the different capsule compartments or solid sub-units may be connected together in different combinations of solid sub-units or solid sub-units and capsule compartments.

For example in one embodiment the respective first and second connectable parts may be respectively interlocking parts. For example the first or second part may be a socket part, and the corresponding second or first connectable part may be a corresponding plug part which fits into the socket with a retaining friction, snap, screw or other kind of interlocking fit. If for example these plug and socket parts are common then any plug part on any solid sub-unit or capsule compartment may interconnect with any socket part on another solid sub-unit or capsule compartment.

In a friction fit for example the plug part may be slightly larger than the socket such that force needs to be applied against the natural resilience and contact friction of the plug and socket parts to cause the plug part to enter the socket, and similar force needs to be applied to separate them. In a snap fit for example the plug and socket parts may be respectively provided with a concavity and a corresponding convexity, such as a ridge and groove, which lock together as the parts are forced together against the natural resilience of the parts. Such a ridge and groove may for example comprise a co-operating circumferential or part circumferential bead and groove, for example located about the circumference of a connectable plug and socket part.

Above-mentioned U.S. Pat. No. 4,576,284 and U.S. Pat. No. 4,738,724 for example, the contents of which are included herein in their entirety by way of reference, disclose a range of interlocking parts of this general type by means of which capsule compartments may be made to interlock together. See for example FIGS. 1, 2 and 3 of U.S. Pat. No. 4,576,284 which discloses interlocking parts by means of which a cap may be retained on the mouth of a capsule, and FIGS. 4-43 of U.S. Pat. No. 4,738,724 which disclose numerous interlocking parts by means of which part capsule shells may interlock and be retained together as an assembled complete capsule.

The above-described first and second connectable parts facilitate assembly of sub-units together in various ways.

For example in a dosage form of the invention comprising a linear disposition of three or more e.g. four, sub-units, an intermediate sub-unit may be provided with one or more connectable parts for example one at each end, which may connect with one or more connectable part on an adjacent intermediate sub-unit. An end sub-unit may be provided with one or more connectable part which may connect with a connectable part on an adjacent intermediate sub-unit and/or with one or more connectable part on another end sub-unit. By means of this two end sub-units may connect together in a dosage form comprising two sub-units, or two end sub-units may be connected to one or more intermediate sub-units. By using common first and second connectable parts on the sub-units the various end and intermediate sub-units may be made such that they may be connected together in various combinations of assembled dosage forms.

One or more sub-unit which is a capsule compartments may for example be substantially tub-shaped, i.e. having a base closed by a base wall, and side walls extending from the base wall (herein referred to as an "upward" direction), and an upper open mouth. With such a construction capsule compartments may connect together by the base of a first compartment fitting into the open mouth of an adjacent second capsule compartment, so as to close the mouth of the adjacent capsule compartment, and such that the base wall of the first compartment physically separates the compartments. In such a construction the base of the first compartment comprises a plug connectable part, and the mouth opening of the second compartment comprises a socket connectable part.

One or more solid sub-unit may for example be shaped so as to fit as a plug into or a cap over the open mouth of an adjacent capsule compartment so as to function as a closure for the mouth. Alternatively one or more solid sub-unit and the outer surface of the base wall of a capsule compartment may be shaped so as to fit adjacent to and connect with each other. For example the base of such a tub-shaped capsule compartment may be provided externally with a plug or socket part and an adjacent solid sub-unit may be provided externally with a corresponding interconnecting socket or plug part. One or more capsule compartment may be formed with a base part that can connect with the mouth opening of an adjacent capsule compartment so as to function as a closure for the mouth in the above-described manner.

For example the base part of the first compartment may be shaped to engage with an adjacent solid sub-unit, e.g. by forming a socket engagement part on the adjacent part of the solid sub-unit which can engage the base of the capsule compartment. A weld between the sub-units may then be formed in the region of contact e.g. between the base of the first compartment or a solid sub-unit, and the mouth of the second compartment. Additionally or alternatively for example the sub-units may be provided with connectable parts to enable a retaining friction, snap, screw or other kind of interlocking fit.

In such an assembly, a capsule compartment may have its mouth opening closed by the base wall of an adjacent compartment or by part of a solid sub-unit fitting into its open mouth in the manner of a plug closure, or over its mouth opening in the manner of a cap closure.

Alternatively a capsule end compartment can be provided with some other type of closure for its mouth opening, particularly if it is connected by its base to an adjacent sub-unit. The closure may for example be made from the same, or a different, polymer than the polymer material of the compartment. This closure may for example comprise an over-cap for example fitting around the outer surface of the side walls of the compartment, as in the general manner disclosed in U.S. Pat. No. 4,196,565 or U.S. Pat. No. 4,250,097 or alternatively the closure may comprise a plug type of closure. Above-mentioned U.S. Pat. No. 4,576,284 discloses some suitable types of closure for capsule compartments which are suitable for use with the present invention. The closure may be retained in place on the mouth opening of its compartment by a weld e.g. as described above, or additionally or alternatively the closure and mouth opening may be provided with features to enable a retaining friction, snap, screw or other kind of interlocking fit.

Adjacent solid sub-units may for example have respective connectable plug and socket parts which can interlock to connect such adjacent parts together in the assembled dosage form.

Alternative ways of assembling and connecting the sub-units are encompassed within the scope of the invention.

For example rather than having an open mouth which is closed by the presence of an adjacent compartment, one or more capsule compartments may be made closed and for example containing the drug substance, and may in this closed form connect in the manner described above with the one or more adjacent sub-units.

For example one or more capsule compartments may be made in the form of two part compartment shells, each part compartment shell comprising a closed end and side walls and having a mouth opening opposite the closed end, which connect together, e.g. by the means discussed above, with their mouth openings facing, to form the capsule compartment, and one or both of the closed ends may have an external connectable part. One or both of the closed ends may connect with an adjacent sub-unit, which may be a solid sub-unit or a capsule compartment, e.g. by the means discussed above. For example if the dosage form comprises a linear assembly of sub-units one or both closed ends of an intermediate capsule compartment(s) may be connectable to an end sub-unit. For example each end sub-unit may be a substantially tub-shaped capsule compartment as described above and may have a mouth opening that is connectable to the closed end in the manner described above, or may be a solid sub-unit.

For example the dosage form may include one or more linker unit positioned between adjacent pairs of sub-units. At least one weld in the dosage form may be between a sub-unit and such a linker unit. Such a linker unit may for example have connectable parts which are connectable to the above-mentioned first and/or second connectable parts on the adjacent sub-units. Suitably to facilitate a linear assembly of sub-units in the dosage form a linker unit may have its connectable parts in opposite linear facing directions. Suitably such a linker unit may comprise a closure for the mouth opening of a capsule compartment, e.g. connecting with the capsule compartment in the manner of a plug or a cap for its mouth opening, and having a connectable part enabling connection to an adjacent sub-unit, e.g. another capsule compartment.

In a specific form the linker may have one or two connectable parts which connect with the mouth opening of a capsule compartment. For example such a linker may have two connectable parts which are opposite facing plug parts and which can connect in a plug and socket manner with the mouth opening of two oppositely-facing capsule compartments to thereby form a capsule-linker-capsule assembly. Suitably welds, e.g. ultrasonic welds, may be formed between both of the capsule compartments and the linker between them in such a dosage form.

When for example a capsule compartment has a closure for its mouth opening, then this closure may comprise a linker having one or more first and/or second connectable parts such that the first or second part on the closure may connect with respectively the second or first part on an adjacent sub-unit in a suitable configuration.

For example in one form such a closure may be provide with two oppositely-facing plug connectable parts which can connect with two socket connectable parts on adjacent sub-units, e.g. the mouth openings of opposite-facing capsule compartments. Such a closure can thereby act as a linker between two capsule compartments with their mouth openings oppositely facing, in a capsule compartment—linker—capsule compartment linear arrangement. For example this arrangement may be an end compartment—linker—end compartment arrangement.

Other ways in which such a linker may be used in a dosage form of the invention will be apparent. For example an intermediate capsule compartment may be in the form of a generally cylindrical shape with two oppositely facing open ends, and two linkers may connect via respectively one each of their connectable parts with an open end of the cylinder, leaving the other connectable part available for connection to respectively another sub-unit.

For forming an ultrasonic weld between adjacent parts of the dosage form of this invention, it is preferred that adjacent parts of the dosage form between which the ultrasonic weld is formed, for example of adjacent contacting, capsule compartments and/or solid sub units, or of adjacent contacting parts of a linker and a capsule compartment or solid unit, in particular of end capsule compartments with a linker in between, are profiled and dimensioned to facilitate an ultrasonic shear joint. A shear joint is one type of weld structure which can be used in ultrasonic welding of polymer materials. Adjacent parts to be brought into contact and welded are dimensioned and profiled to provide a small initial contact area, then a controlled interference occurs along the joint as the parts collapse together under the application of ultrasonic energy.

For example a suitable profile is provided by plug and socket connectable parts comprising engaging tenon parts (e.g. opposite facing complementary steps), where the length of one tenon is less than the length of the other tenon part, and under the ultrasonic welding operation the material of the parts can collapse until the tenon parts longitudinally engage.

The multicomponent dosage form of this invention comprising a capsule compartment—linker—capsule compartment in a linear arrangement and connected together by means of at least one ultrasonic weld formed between a capsule compartment and the linker is a particular form of this invention, and some preferred features of this form are discussed below.

Advantageous features of the capsule compartments have been devised to facilitate assembly and/or ultrasonic welding of the dosage form of this invention. The wall of the capsule compartment is preferably ca. 0.1-0.8 mm, especially 0.3-0.5 mm, thick, at least in the cylindrical side walls of the compartment, this thickness being generally found suitable as a minimum to reduce the risk of damage to the compartment by the ultrasonic energy during the welding operation. A thickness of 0.45±0.05 mm is particularly preferred as a balance between strength for welding and drug content release. The end compartments in such a two compartment capsule are suitably each in the shape of a cylinder having one open end and one closed end. The closed end is suitably closed by a generally rounded, e.g. hemispherical end wall, e.g. an open ended "bucket" or "tub" shape. Suitably the side walls taper gently in a shallow conical fashion, the cross section being greatest at the open end (e.g. inter alia to facilitate removal from an injection mould). Suitably the central part of the rounded end of such a bucket or tub shape may be flattened to facilitate the application of ultrasonic energy during the welding operation.

Preferably at least one, preferably both, of the connectable parts of the linker is a plug part which fits in a plug-and-socket manner into the open end of a capsule compartment. Therefore such a plug part is typically a cylindrical shape, corresponding closely to the internal shape of the open end of a capsule compartment adjacent to the open end.

Preferably the linker is in the form of a solid wall part with oppositely facing plug connectable parts, oppositely facing end surfaces of the plug parts extending generally transverse to the longitudinal direction of the linker. Preferably each plug part is a snug friction fit into the open end of a capsule compartment. Preferably each plug part is provided with an abutment surface to define and limit the extent to which each plug part can extend into the open end of a capsule compartment by abutting against the rim of the open end of a capsule compartment when the plug part extends to a suitable extent into the capsule mouth.

In a preferred construction, the linker comprises a generally cylindrical solid body, its opposite facing ends being plug parts, with two oppositely facing abutment surfaces each being a surface of a ledge formed around the circumference of the cylindrical body and generally planar in a plane perpendicular to the length direction. Such a ledge may typically be ring shaped with its plane perpendicular to the longitudinal direction of the capsule. With such a linker the assembled dosage form may comprise two capsule compartments each in the shape of a cylinder having one open end and one closed end (e.g. the above-described tub or bucket shapes), with their open ends in an opposite facing relationship, with a linker between them with each of the opposite facing plug parts of the linker fitting in a plug-and-socket manner into the open end of a capsule compartment, with an ultrasonic weld formed between a plug part and/or an abutment surface of the linker and the compartment wall in the vicinity of the open end, e.g. the rim of the open end.

Another assembled dosage form may comprise three capsule compartments, two being end compartments each in the shape of a cylinder having one open end and one closed end, with their open ends in an opposite facing relationship, with an intermediate compartment longitudinally between the two end compartments, with a linker between each end compartment and the intermediate compartment and with each of the opposite facing plug parts of the linker fitting in a plug-andsocket manner into the open end of a capsule compartment, with an ultrasonic weld formed between a plug part and/or an abutment surface of the linker and the compartment wall in the vicinity of the open end, e.g. the rim of the open end.

Advantageous features of the linker have also been devised to facilitate assembly and/or ultrasonic welding of the dosage form of this invention.

Preferably the linker is overall in the form of a cylindrical body flattened in its length direction, for example having diameter:length ratios in the range 4:1 to 1.5:1. The body may have an end surface which is substantially planar over at least 50% of its extent to facilitate ultrasonic welding as such a planar surface is found to assist in the transmission of ultrasonic energy from a welding horn to the area where the ultrasonic weld is to be formed when the plug part of the linker is fitted into the open end. For example such a planar surface may be a ring-shaped surface surrounding a central concavity. In a multi-capsule compartment of this invention which is of the order of size of conventional capsules it appears to be advantageous for such a planar surface to extend continuously over a dimension of at least 2 mm, e.g. over at least 4 mm$^2$ area to allow ultrasonic energy to be applied to such a surface by means of an ultrasonic welding horn whilst minimising the risk of damaging, e.g. cracking, the linker. Also it appears to be advantageous for the linker to have a length of at least 2 mm to allow ultrasonic energy to be applied to the linker by means of an ultrasonic welding horn whilst minimising the risk of damaging the linker. Similarly with a capsule compartment wall the shape of a cylinder having one open end and one closed end, it is again preferred that at least 5% of the outer surface of the closed end is substantially planar, to facilitate the application of ultrasonic energy. Again it appears to be advantageous for such a planar surface to extend continuously over a dimension of at least 2 mm e.g. over at least 4 mm$^2$ area.

A plug part of such a linker may typically have a length of up to ca. 45% of the length of the linker, e.g. up to ca. 25%.

Generally for the ultrasonic welding operation to form an ultrasonic weld in a multicomponent dosage form of the above-described type comprising a capsule compartment—linker—capsule compartment in a linear arrangement, of a size typical of a pharmaceutical capsule, a conventional (e.g. Branson, Rainbow) ultrasonic welding machine operating at 20-40 KHz can produce a suitable weld in ca. 500 ms.

The assembly and ultrasonic welding of the multicomponent dosage form of the above-described type comprising a capsule compartment—linker—capsule compartment in a linear arrangement may comprise the steps of first filling a first capsule compartment with a suitable quantity of drug substance; insertion of a first plug part of a linker into the open end of the first capsule compartment and welding this in place; filling a second capsule compartment containing a suitable quantity of drug substance; insertion of the opposite, second, plug part of the linker into the open end of the second capsule compartment and welding the linker and second capsule compartment together. The weld is preferably an ultrasonic weld.

The parts of the dosage form of this invention, e.g. a capsule compartment wall, a solid sub-unit, or a closure or linker as described above may comprise any pharmaceutically acceptable polymer (and adhesive material if adhesive welds are formed) which is generally regarded as safe, e.g. for oral injestion and is capable of being formed into the required shape of a capsule compartment wall, a solid sub-unit, or a closure or linker as described above. A preferred method of forming the polymer material into the desired shape is injection moulding, which may be a hot or cold runner injection moulding process. Suitable injection moulding machines for such a process are known.

In the process of injection moulding a fluid polymer is injected under pressure into a precisely made die cavity in a mould block. Injection moulding processes can enable the sub-units to be made with the precision necessary to achieve connection by tight friction-fit or snap-fit interlocking and to maintain suitable contact between adjacent parts to facilitate a weld. Suitable techniques of injection moulding are known from for example the art of manufacture of small plastic components e.g. small parts of LEGO™ toys. Processes such as those described in Cuff. G and Raouf. F (op. cit.) may be used to manufacture such solid sub-units and capsule compartments via injection moulding.

Consequently the invention also provides a moulding process, for example an injection moulding or powder compression process, wherein sub-units, including the solid sub-units and capsule compartments of the dosage form are made in respective mould cavities.

The invention also provides a mould or die, for example an injection mould or powder compression mould or die suitable for use in this moulding process. Such a mould or die may have a mould cavity corresponding to the shape of the sub-unit. Moulds may be made by known metal engraving processes such as spark-erosion, and it is generally preferred to use moulds made from pharmaceutically acceptable metals e.g. steels of the type known for use in tablet compression dyes.

Suitable polymers for the parts of the dosage form of this invention include: polyvinyl alcohol (PVA), natural polymers (such as polysaccharides like pullulan, carrageenan, xanthan, chitosan or agar gums), polyethylene glycols (PEG), polyethylene oxides (PEO), mixtures of PEGs and PEOs, hydroxypropylmethylcellulose (HPMC), methylcellulose, hydroxyethylcellulose, hydroxyethyl methylcellulose, hydroxypropylcellulose, methacrylic acid copolymer (such as Eudragit E™, Eudragit L™ and/or Eudragit S™), ammonium methacrylate copolymers (such as Eudragit RL™ and/or Eudragit RS™), carboxymethylcellulose, povidone (polyvinyl pyrrolidone), polyglycolysed glycerides (such as Gelucire 44/14™, Gelucire 50/02™, Gelucire 50/13™ and Gelucire 53/10™), carboxyvinyl polymers (such as Carbopols™), polyoxyethylene-polyoxypropylene copolymers (such as Poloxamer 188™).

Acrylic and/or methacrylic acid-based polymers which are soluble in intestinal fluids and which can be formed into capsules are for example disclosed in U.S. Pat. No. 5,705,189 (Roehm GmbH) the content of which is incorporated herein by reference. The Eudragit™ polymers discussed above for example are extrudable and may for example be plasticised with e.g. triethyl citrate, or glyceryl monostearate.

It is also known to form solid bodies suitable for the solid sub-units of this invention using processes of powder compression. For such processes amylose, cross-linked amylose and amylose-pectin combinations may be suitable.

Preferred polymers are orally ingestible polymers and include polyvinyl alcohol, hydroxypropyl methyl cellulose, and other cellulose-based polymers. Preferred polymers also include polymer materials which preferentially dissolve or disintegrate at different points in the digestive tract. Such polymers include the known acrylic and/or methacrylic acid-based polymers which are soluble in intestinal fluids, e.g. the Eudragit™ series of commercially available polymers. Examples of these include Eudragit E™, such as Eudragit E 100™, which preferentially dissolves in the more acid pH of the stomach, or enteric polymers such as Eudragit L™ and/or Eudragit S™ which preferentially dissolve in the more alkaline pH of the intestine, and Preferred polymers also include polymers which dissolve slowly, e.g. a predetermined rate in the digestive tract, such as Eudragit RL™, e.g. Eudragit RL 100™, and/or Eudragit RS™ e.g. Eudragit R100™, and/or blends of such Eudragit™ polymers.

The polymer material(s) may include other substances to modify their properties and to adapt them to various applications, including for example the following general classes of substances. Surfactants, such as Polysorbate 80™, sodium lauryl sulphate, and Polyoxyl 40™ hydrogenated castor oil. Absorption enhancers, such as Labrasol™, Transcutol™; glidants, such as stearyl alcohol, talc, magnesium stearate, silicon dioxide, amorphous silicic acid, fumed silica, Simeticone™; plasticizers, such as triethyl citrate, acetyl triethyl citrate, tributyl citrate, acetyl tributyl citrate, glyceryl monostearate, diethyl phthalate, dibutyl phthalate, propylene glycol, triacetin and castor oil; substances for release modification, such as ethyl cellulose and cellulose acetate phthalate; disintegrants, such as sodium starch glycollate, croscarmellose sodium, crospovidone (cross-linked polyvinyl pyrrolodone), colouring agents, flavouring agents and sweetening agents.

The sub-units may additionally include materials in the polymer materials of which they are made to enhance the ease with which they can be welded together. The sub-units may additionally be provided with constructional features and/or include materials in the polymer materials of which they are made to enhance the ease with which they can be welded together, e.g. opacifier materials such as carbon (e.g. 0.2-0.5%), iron oxides or titanium dioxide (e.g. 0.5-1.0%) to help the polymer to absorb laser energy. Such opacifier materials are generally regarded as safe.

For example each of a plurality of sub units, e.g. of capsule compartments, solid sub-units, or combinations thereof may comprise the same or different polymer.

For example each of a plurality of sub-units, e.g. of capsule compartments, solid sub-units, or combinations thereof may comprise the same or different drug substance.

For example each sub-unit may contain the same drug substance but releasable in the gastro-intestinal tract of the patient at a different rate, at different times after administration to the patient or at different places in the patient's gastro-intestinal system. Alternatively each sub-unit may contain a different drug substance, each of which may be released at the same or a different rate or time after administration or place in the patient's gastro-intestinal system.

For example two or more sub-units, e.g. two capsule compartments, may each contain different drug substances, and/or different drug substance formulations, and/or the same drug in different formulations, so that a combination of two or more drug substances or formulations may be administered to a patient.

The dosage form of this invention enables the assembly together of sub-units which differ in their drug content and/or drug content release characteristics to provide a dosage form tailored to specific administration requirements.

The dimensions and shape of each of the sub-units and hence of the overall assembled dosage form may be determined by the nature and quantity of the material to be contained therein and the intended mode of administration and intended recipients. For example a dosage form intended for oral administration may be of a shape and size similar to that of known capsules intended for oral administration.

The dosage form is particularly suitable for presentation as an oral dosage form containing one or more drug substances suitable for oral administration, and appears to be suitable for all types of such drug substance.

As explained in Cuff G. and Raouf F. (op.cit.), in the matrix of solid sub-units the drug substance may be present in various states. For example it may comprise discrete particles dispersed in the matrix, for example in the case of particles that do not readily dissolve in the fluid polymer. Alternatively the drug substance may be present as a solid solution in the solid polymer of the matrix. Alternatively some of the drug substance may comprise discrete particles and some may be present as a solid solution in the polymer. When two or more solid sub-units are present the drug substance present in each solid sub-unit may be in the same or in different states, e.g. having different drug substance release characteristics.

The drug substance(s) contained in any capsule compartment may be present in any suitable, e.g. conventional, form, e.g. as a powder, granules, compact, microcapsules, gel, syrup or liquid provided that the capsule compartment wall material is sufficiently inert to the liquid content of the latter three forms. The contents of the compartments, e.g. drug substances, may be introduced into the compartments by standard methods such as those used conventionally for filling capsules, such as dosating pins or die filling.

The sub-units may differ from each other in their drug content release characteristics, and this may be achieved in various ways.

For example one or more solid sub-units and/or capsule compartments may be substantially immediate release, i.e. releasing their drug content substantially immediately upon injection or on reaching the stomach. This may for example be achieved by means of the matrix polymer or the capsule compartment wall dissolving, disintegrating or otherwise being breached to release the drug content substantially immediately. Generally, immediate-release sub-units are preferably provided by being capsule compartments.

For example one or more solid sub-units and/or capsule compartments may be sustained-release sub-units. Preferably these are solid sub-units, as a bulk matrix of polymer is likely to dissolve or disperse more slowly to release its drug content that a thin walled capsule.

For example one or more solid sub-units and/or capsule compartments may be pulsed-release sub-units for example releasing their drug content at a specific predetermined point in a patient's gastro-intestinal system. This may be achieved by the use of polymer materials which dissolve or disperse only at defined pH environments, such as the above mentioned Eudragit™ polymers.

In the case of the above-described linear arrangement of sub-units, suitably one of the end sub-units, particularly a capsule compartment may be a substantially immediate-release compartment, so that the disruption of this end sub-unit has little or no influence on the other sub-units, e.g. the other end sub-unit or the intermediate sub-unit(s), in the assembly. In such a case the other end and the intermediate sub-unit(s) may be delayed or pulse release sub-units, i.e. releasing their drug content at a delayed time after administration. For example in the case of oral administration these delayed release sub-units may release their drug content in the stomach, small or large intestine.

For example in the above-described capsule compartment-linker-capsule compartment dosage form one capsule compartment may be effectively immediate release and the other may be sustained, delayed or pulsed release. To achieve this for example one capsule compartment may be made of polymer materials which cause the capsule compartment to release its drug content in the stomach or upper part of the digestive tract, and the linker (acting as a closure for the second compartment) and the second compartment itself may be made of materials e.g. the above described enteric polymers, which release their drug content only in the intestinal environment.

Determination of the time or location within the gastrointestinal tract at which a sub-unit releases its drug substance content may be achieved by for example the nature of the sub-unit material, e.g. a solid sub-unit matrix polymer or a capsule compartment wall material, or in the case of an end compartment which is closed by a closure, by the nature of the closure material. For example the wall of different, e.g. adjacent, compartments may be made of polymers which are different or which otherwise differ in their dissolution or disintegration characteristics so as to endow different compartments with different drug release characteristics. Similarly for example the polymer matrix material of different, e.g. adjacent, solid sub-units may be made of polymers which are different or which otherwise differ in their dissolution or disintegration characteristics so as to endow different solid sub-units with different drug release characteristics.

For example the matrix, wall or closure material may be a polymer which dissolves or disperses at stomach pH to release the drug substance in the stomach. Alternatively the wall material of different compartments may differ so that different compartments have different release characteristics.

For example a solid sub-unit or a capsule compartment may have respectively a matrix or a wall or a closure comprising an enteric polymer which dissolves or disperses at the pH of the small or large intestine to release the drug substance in the intestine. Suitable such polymers have been described above, for example with reference to U.S. Pat. No. 5,705,189.

Additionally or alternatively the wall material may differ in thickness between compartments so that thicker walled compartments disrupt more slowly than thinner walled compartments.

Additionally or alternatively the compartment walls or the closure may have areas or points of weakness which preferentially dissolve and may thereby determine the time of onset and/or rate of release of the drug substance content. For example such points of weakness may comprise holes, e.g. small holes, e.g. laser-drilled holes in the compartment wall or the closure, these holes being closed and/or covered with a film of a polymer material that dissolves at a pre-determined point in the digestive tract, for example an enteric polymer material. For example such points of weakness may comprise thinned parts in a capsule compartment wall formed during the moulding operation in which the capsule compartment is formed.

The sub-units may additionally or alternatively have surface or other constructional features which modify their drug release characteristics. For example solid sub-units may be provided with internal cavities or channels to create a large surface area. For example solid sub-units may be in the form of hollow cylinders, donuts, or toroids, which shapes are known to tend towards first-order dissolution or erosion in liquid media and correspondingly to tend toward first-order release of drug content dispersed therein.

The invention will now be described by way of example only with reference to:

FIG. 1 which shows a longitudinal sectional view of a dosage form of the invention assembled together.

Figure 2:
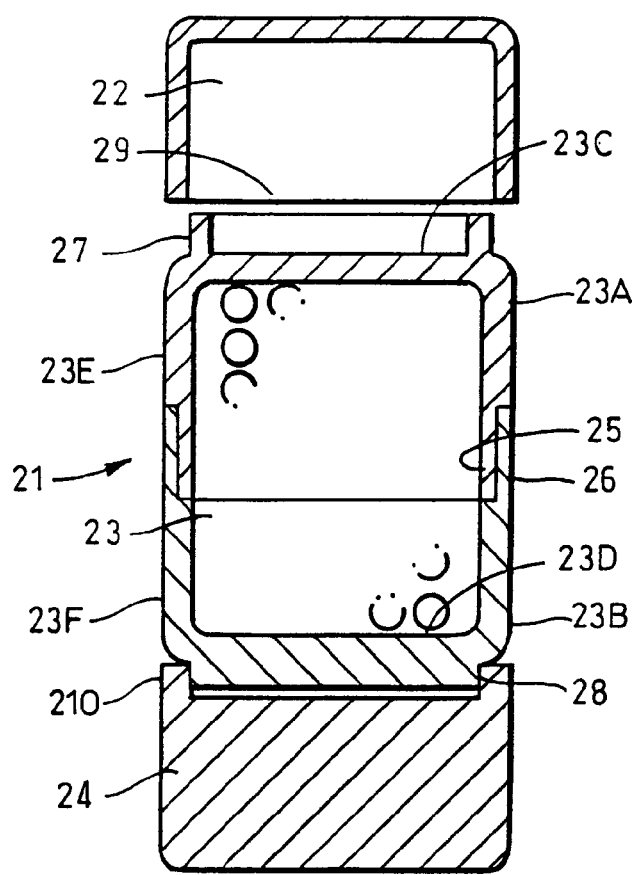

FIG. 2 which shows a longitudinal sectional view of another dosage form of the invention assembled together.

Figure 3:
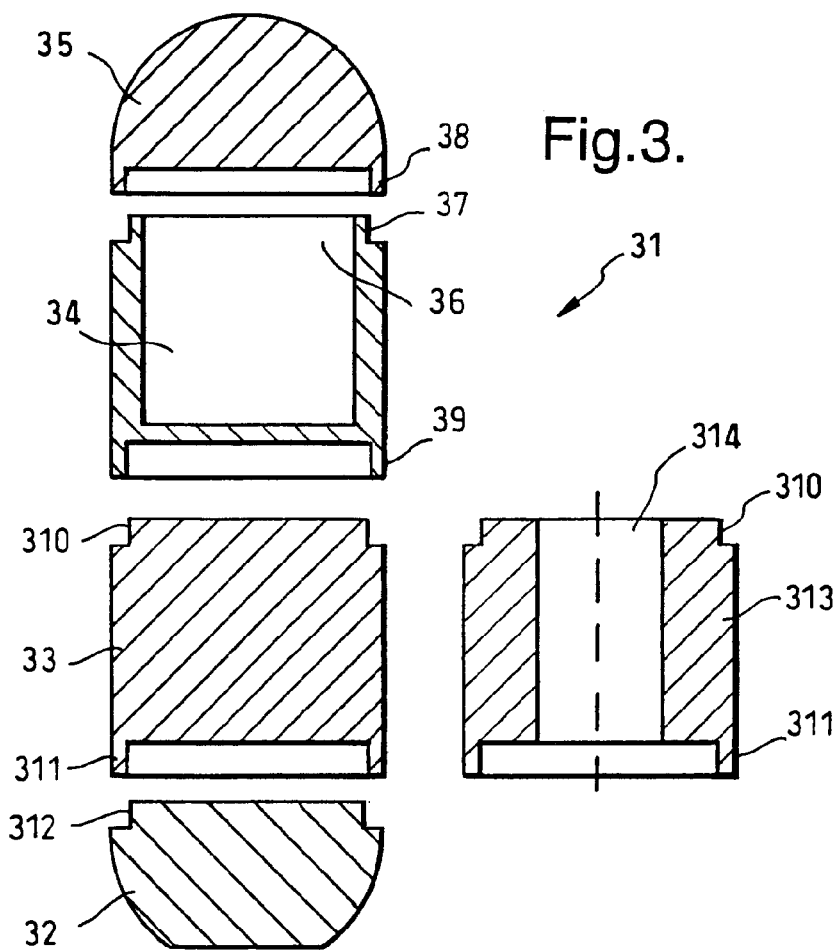

FIG. 3 which shows a longitudinal sectional view of another dosage form of the invention assembled together.

Figure 4:
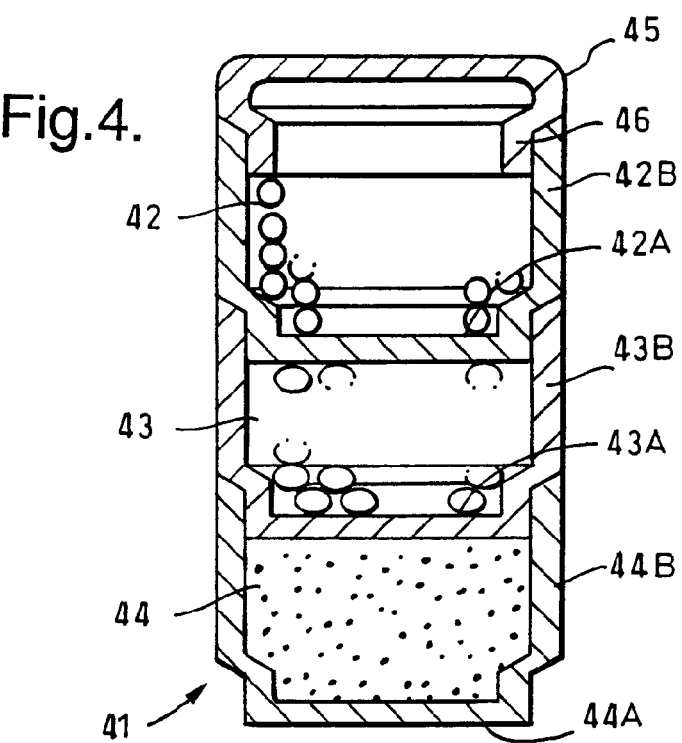

FIG. 4 which shows a longitudinal sectional view of a dosage form of the invention assembled together.

Figure 5:
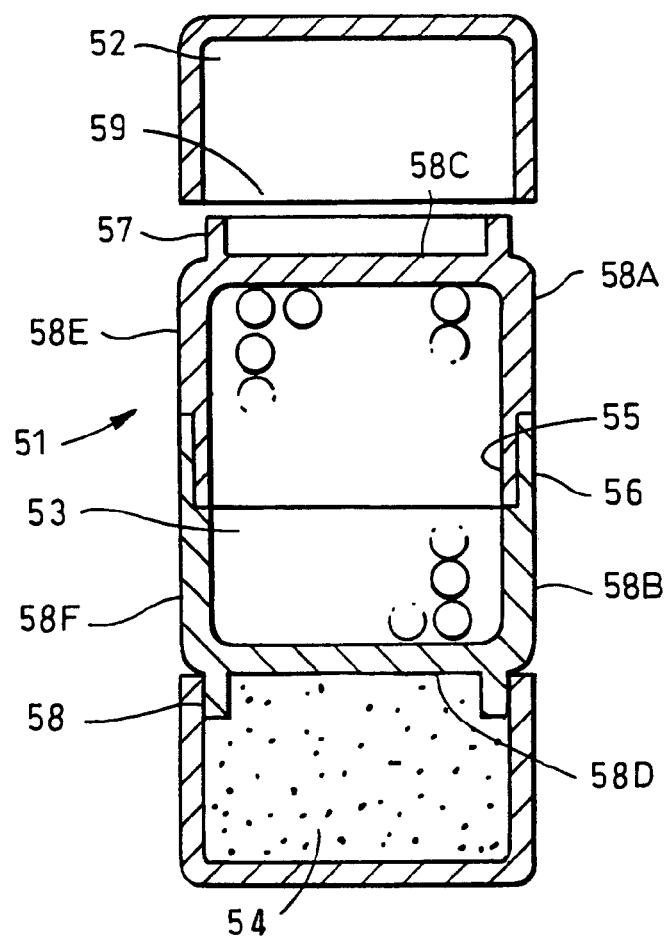

FIG. 5 which shows a longitudinal sectional view of another dosage form of the invention assembled together.

FIG. 6 which shows longitudinal and cross sections, and an enlarged part view of another dosage form of the invention.

Figure 6A:
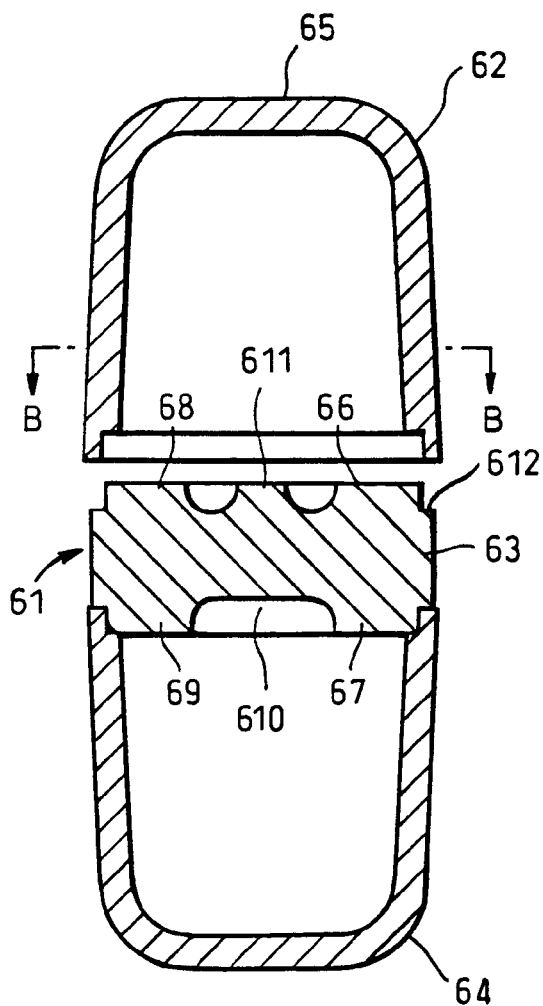
Figure 6B:
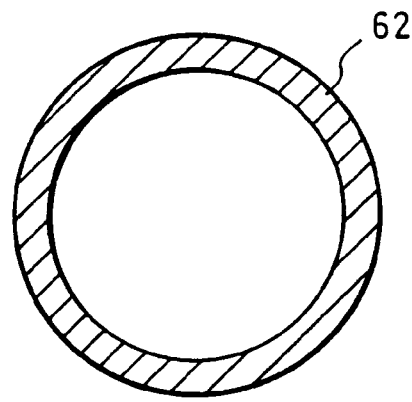
Figure 6C:
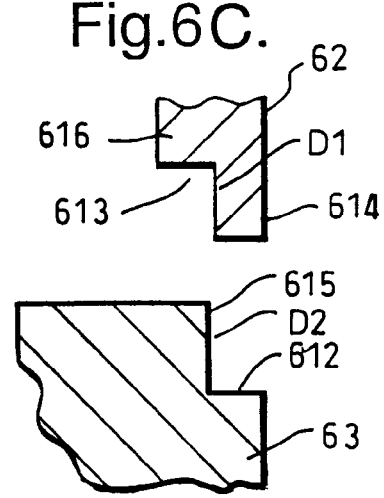
Figure 7:
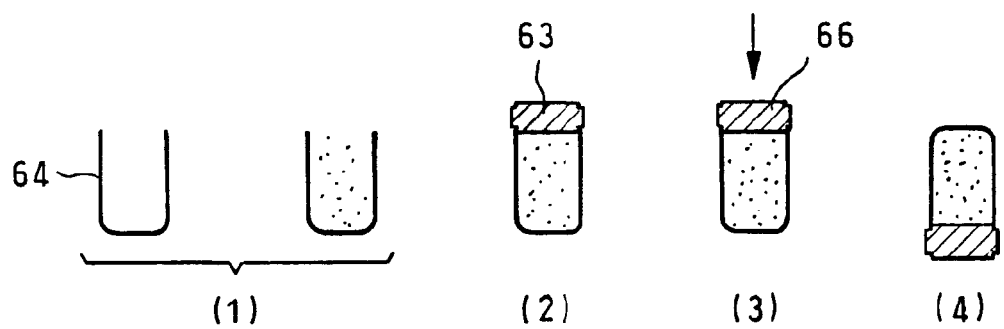
Figure 7:
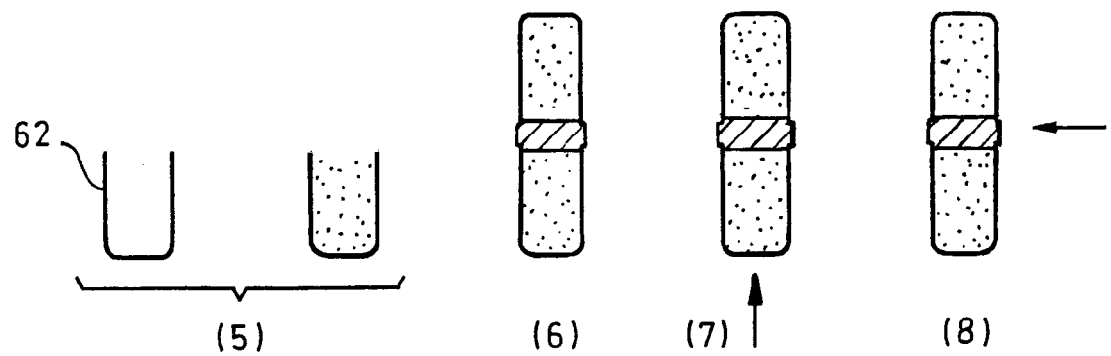

FIG. 7 which shows an assembly sequence of a dosage form of FIG. 6.

Referring to FIG. 1, a dosage form 11 is shown comprising three sub-units 12, 13, 14 linearly disposed in the assembled dosage form, in an arrangement comprising two end compartments 12, 14 at opposite ends of the line, and one intermediate solid sub-unit 13. The compartments 12 and 14 and the solid sub-unit 13 are substantially cylindrical. The compartments 12 and 14 are substantially tub-shaped, i.e. each having a base closed by a base wall 12A, 14A, and each having side walls 2B, 4B extending upward from the base wall 12A, 14A, and an upper open mouth. Each of the compartments 12 and 14 is made of polyvinyl alcohol polymer by injection moulding.

The solid sub-unit 13 is also substantially cylindrical, and has its base end 13A formed into a plug shape capable of engaging with and thereby closing the open mouth of either compartment 12 or 14. As shown in FIG. 1 the base end 13A of solid sub-unit 13 fits into and is in engagement with the mouth opening of compartment 14. The upper end of solid sub-unit 13 has its upper end 13B formed into a socket connector capable of engaging with the shape of the base 12A or 14A of capsule compartment 12 or 14, as shown in FIG. 1 being in engagement with the base of compartment 12.

The compartments 12, 14 and solid sub-unit 13 connect together by the base 12A of compartment 12 fitting into the upper socket 13B of adjacent solid sub-unit 13, and the base 12A of the solid sub-unit 13, fitting into the open mouth of adjacent compartment 14 so as to close its mouth. In this assembly of sub-units 12, 13, 14 the base part of an upper sub-unit 12, 13 comprises a plug part and the mouth opening or upper socket of a lower sub-unit respectively 13, 14 comprises a socket.

Compartment 14 is an end compartment 13 and has its mouth opening closed by the base end 13A of solid sub-unit 13. The other upper end compartment 12 is closed by a closure 15 having a plug part 16 which is dimensioned to fit into the mouth opening of the compartment 12.

The base parts 12A and 13A and the plug part 16, fit into the respective mouth openings of the compartments 12 and 14. A thermal weld is formed between the base parts 12A and 13A, the plug part 16, and the respective mouth openings and upper socket of the compartments 12, 14 and the solid sub-unit 13 at the region where these parts are in contact. Each of the base parts 12A, 13A, and the plug part 16, and the corresponding respective mouth openings and upper socket of the compartments 12, 13 and 14 may additionally or alternatively be provided with features (not shown) such as a convex circumferential bead and a corresponding circumferential groove into which the bead may fit, such that the base part 12A, 13A, the mouth openings of the compartments 12 and 14, the upper socket 13B and the plug part 16 and mouth opening of compartment 12 may connect together by a snap fit interlocking engagement overcoming the natural resilience of the polymer material of the base part and mouth opening.

A thermal weld may be formed between the base parts 12A and 13A, the plug part 16, and the respective mouth openings and upper socket of the compartments 12, 14 and the solid sub-unit 13, by directing a laser beam to the region where these parts are in contact.

The base parts 12A, 13A, 14A of the compartments 12, 13, 14, the mouth openings of the compartments 12 and 14, the upper socket 3B and the plug part 16 are all of common dimensions so that the compartments 12 and 14 and the solid sub-unit may be fitted together in other linear combinations, and so that the plug 15 may be used to close the mouth opening of the other compartments 14.

Similarly, two or more than the three sub-units 12, 13 or 14, may be connected together in an analogous manner to that shown in FIG. 1.

FIG. 2 shows another dosage form assembly 21. This assembly 21 also comprises three sub-units 22, 23, 24 in a linear assembly of an end compartment 22, an intermediate compartment 23 and an end solid sub-unit 24. The intermediate compartment 23 is made in the form of part compartment shells 23A and 23B, each part shell 23A, 23B comprising a closed end 23C and 23D and side walls 23E and 23F with a mouth opening opposite each closed end 23C and 23D. The mouth openings of the two part shells 23A and 23B are each provided respectively with a plug connectable part 25 and a socket connectable part 26. These part shells 23A, 23B connect together with their respective plug and socket parts 25 and 26 connecting to form the capsule compartment 23. Both of the closed ends 23C, 23D are externally provided with connectable parts 27, 28.

The end compartment 22 is in the form of a tub-shaped compartment and has a mouth opening 29, which comprises a socket part that corresponds in shape with connectable part 27 on the intermediate compartment 23 to connect the assembly 21 together.

The end solid sub-unit 24 is formed as a substantially cylindrical body, having a connectable part 210 in the form of a socket engageable with either of the connectable parts 27 or 28 on intermediate capsule compartment 23. As shown in FIG. 2 the connectable part 210 on solid sub-unit 24 is connected to the part 28 on capsule compartment 23.

As with the dosage form of FIG. 1, a thermal weld is formed between the parts 25, 26, 27, 29, 28 and 210 at the region where these parts are in contact. Each of these parts 25, 26, 27, 29, 28 and 210 may additionally or alternatively be provided with features (not shown) such as respectively a convex circumferential bead and a circumferential groove into which the bead may fit, such that these interlocking parts may connect together by a snap fit engagement.

FIG. 3 shows another dosage form assembly 31. This assembly 31 comprises four sub-units 32, 33, 34, 35 in a linear assembly of an end solid sub-unit 32, an intermediate solid sub-unit 33, an intermediate capsule compartment 34 and an end solid sub-unit 35. The intermediate capsule compartment sub-unit 34 has a mouth opening 36, and the immediately adjacent rim 37 of this mouth opening 36 is formed as a plug connectable part. The end solid sub-unit 35 is substantially hemispherical and is formed as a closure cap for the tub-shaped intermediate capsule compartment 34, being formed at its lower end as a socket connectable part 38 which fits in a sealing engagement with the part 37. The closed lower end 34A of compartment 34 is externally provided with a socket connectable part 39.

The intermediate solid sub-unit 33 has its upper end formed as a plug connectable part 310 engageable with the part 39 of the compartment 34, and a lower end formed as a socket connectable part 311.

The end solid sub-unit 32 is in the form of a rounded bottomed cylinder having a plug connectable part 312 part that corresponds in shape with connectable part 311 on the intermediate compartment 33. Each of these parts 37, 38, 39, 310, 311, 312 may additionally or alternatively be provided with features (not shown) such as respectively a convex circumferential bead and a circumferential groove into which the bead may fit, such that these interlocking parts may connect together by a snap fit engagement.

Designated 313 is an alternative construction of the intermediate solid sub-unit 33, parts common with the sub-unit 33 being numbered correspondingly. The sub-unit 313 has an internal cylindrical bore 314 so that the sub-unit 313 is of a generally hollow cylindrical shape. The bore 314 may alternatively be of a longitudinally tapering e.g. generally cylindrical shape.

By connection of the various connectable parts 37, 38, 39, 310, 311, 312 the assembly 31 may be connected together along the axis shown.

FIG. 4 shows a dosage form 41 comprising three capsule compartments 42, 43, 44 linearly disposed in the assembled dosage form, in an arrangement comprising two end compartments 42, 44 at opposite ends of the line, and one intermediate compartment 43. All of the compartments 42, 43, 44 are substantially cylindrical but with an oval cross section across the longitudinal axis. The compartments 42, 43, 44 are substantially tub-shaped, i.e. each having a base closed by a base wall 42A, 43A, 44A, and each having side walls 42B, 43B, 44B extending upward from the base wall 42A, 43A, 44A, and an upper open mouth.

Each of the compartments 42, 43 and 44 is made of a polymer such as polyvinyl alcohol polymer by injection moulding.

The compartments connect together by the base 42A, 43A of a first compartment 42, 43 fitting into the open mouth of an adjacent second compartment respectively 43, 44 so as to close the mouth, and such that the base wall 42A, 43A of the first compartment 42, 43 physically separates the first and second compartments 42, 43 and 44. In this assembly of compartments 42, 43, 44 the base part of an upper compartment 42, 43 comprises a plug part and the mouth opening of a lower compartment respectively 43, 44 comprises a socket.

Compartment 44 is an end compartment and has its mouth opening closed by the base wall 43A of compartment 43. The other end compartment 42 is closed by a closure 45 having a plug part 46 which is dimensioned to fit into the mouth opening of the compartment 42.

The base parts 42A and 43A, and the plug part 46, fit into the respective mouth openings of the compartments 43, 44 and 42. A weld is formed between the base parts 42A and 43A, the plug part 46, and the respective mouth openings of the compartments 43, 44 and 42, for example by the application of local heating or an ultrasonic horn (not shown) to the region where these parts are in contact. Each of the base parts 42A, 43A, and the plug part 46, and the corresponding mouth openings of the compartments 43, 44 and 42 may additionally or alternatively be provided with features (not shown) such as a convex circumferential bead and a corresponding circumferential groove into which the bead may fit, such that the base part 42A, 43A and mouth openings of the compartments 43 and 44, and the plug part 46 and mouth opening of compartment 42 may connect together by a snap fit interlocking engagement overcoming the natural resilience of the polymer material of the base part and mouth opening.

The base parts 42A, 43A, 44A of the compartments and the mouth openings of the compartments 42, 43, 44, and the plug part 46 are all of common dimensions so that the compartments 42, 43 and 44 may be fitted together in other linear combinations, and so that the plug 45 may be used to close the mouth opening of any of the other compartments 42, 43 or 44.

Similarly, two or more than the three compartments 42, 43 or 44, may be connected together in an analogous manner to that shown in FIG. 4.

FIG. 5 shows another dosage form assembly 51. This assembly 51 also comprises three compartments 52, 53, 54 in a linear assembly of two end compartments 52, 54 and an intermediate compartment 53. The intermediate compartment 53 is made in the form of part compartment shells 53A and 53B, each part shell 53A, 53B comprising a closed end 53C and 53D and side walls 53E and 53F, with a mouth opening opposite the closed end. The mouth openings of the two part shells 53A and 53B are each provided respectively with a plug connectable part 55 and a socket connectable part 56. These part shells 53A, 53B connect together with their respective plug and socket parts 55 and 56 connecting to form the capsule compartment 53. Both of the closed ends 53C, 53D are externally provided with connectable plug parts 57, 58.

Each end compartment 52, 54 is in the form of a tub-shaped compartment and has a mouth opening, e.g. 59 being that of compartment 52, which comprises a socket part that corresponds in shape with the connectable plug parts 57, 58 on the intermediate compartment 53 to connect the assembly 51 together.

As with the dosage form of FIG. 4, a weld is formed between the parts 55, 56, 57, 58 and the respective mouth openings of the compartments 52, 54, by the application of local heating or an ultrasonic horn (not shown) to the region where these parts are in contact. Each of these parts 55, 56, 57, 58 and the respective mouth openings of the compartments 52, 54 may additionally or alternatively be provided with features (not shown) such as respectively a convex circumferential bead and a circumferential groove into which the bead may fit, such that these interlocking parts may connect together by a snap fit engagement.

Each of the compartments 42, 43, 44, 52, 54 in FIGS. 4 and 5 may be made of the same or different polymer and may have the same or different drug release characteristics. The intermediate compartments respectively of FIGS. 1 and 2 are more suitable for a modified release compartment, as dissolution or disruption of the end compartments 2, 4, 7 and 9 before the intermediate compartments 3 and 8 can occur without disturbance of these intermediate compartments.

Each of the compartments 42, 43, 44, 53, 54 and 55 in FIGS. 4 and 5 contains the same or different drug substance and/or formulation. This may for example be in the form of powder, granulates, or other solid forms. Alternatively the compartments may contain liquid, gel etc. formulations (not shown).

FIG. 6 shows another dosage form assembly 61. As shown in the longitudinal section FIG. 6A and the cross section FIG. 6B this comprises an assembly of an end capsule compartment 62—linker 63—end capsule compartment 64 in a linear arrangement. Each end compartment 62, 64 is suitably in the shape of a cylinder having one open end and one closed end. The closed end is in the form of a generally hemispherical end wall, forming an open ended "bucket" or "tub" shape. The side walls of each capsule compartment taper gently in a shallow conical fashion, the cross section being greatest at the open end. The central part 65 of the rounded end of each compartment 62, 64 is flattened over at least 5% of the end surface area to facilitate the application of ultrasonic energy during the welding operation. The wall of each capsule compartment 62, 64 is ca. 0.4±0.05 mm thick in the cylindrical side walls of the compartment.

The "linker" 63 is provided in the form of a solid wall with oppositely facing surfaces 66, 67 extending generally transverse to the longitudinal direction of the linker, being the end surfaces of oppositely facing plug connectable parts 68, 69 formed at each of its longitudinal ends. The linker 63 is a generally cylindrical body flattened in its length direction with a diameter:length ratio ca. 3:1. In a specific embodiment the diameter of the linker 63 is ca 7.5 mm, and its length ca. 3.0 mm. The end surfaces 66, 67 are substantially planar over at least 50% of their extent to facilitate application of ultrasonic energy thereto in the welding operation. The planar surface 66, 67 is a ring-shaped surface surrounding a central concavity 610 on each face, in which is the residue 611 of the injection moulding runner. The planar surface 66, 67 extends continuously over a dimension of at least 2 mm, i.e. having a surface area of at least 4 $mm^2$. Each plug part 68, 69 is a snug friction fit into the open end of a capsule compartment 62, 64. Each plug part 68, 69 is provided with an abutment surface 612 each being a surface of a ledge formed around the circumference of the cylindrical body 63. The ledge 612 is ring shaped with its plane perpendicular to the longitudinal direction of the capsule. The ledge 612 defines and limit the extent to which each plug part 68, 69 can extend into the open end of a capsule compartment 62, 64 by abutting against the rim of the open end of a capsule compartment 62, 64. In the specific embodiment the ledge 612 is ca 0.3 mm wide in the direction across the length direction.

An ultrasonic weld is formed between each plug part 68, 69 and/or an abutment surface 612 of the linker 63 and the compartment wall 62, 64 in the vicinity of the open end, e.g. the rim of the open end. The lower compartment 64 is shown formed in this way, the upper compartment 62 being shown disassembled.

For forming an ultrasonic weld between adjacent contacting parts of the capsule compartments 62, 64 and the linker 63 these parts are profiled and dimensioned to facilitate an ultrasonic shear joint, as shown enlarged in FIG. 6C. The plug 68 and socket 613 connectable parts comprise interlocking tenon parts 614, 615, where the length of one tenon 614 (D1 ca. 0.2-0.3 mm) is less than the length (D2 ca. 0.5-0.6 mm) of the other tenon part 615, and under the ultrasonic welding operation the material of the capsule compartment 62 in the region 616 can collapse until the tenon parts longitudinally engage to form the ultrasonic weld between the capsule compartment 62 and the linker 63. The weld between the linker 63 and the compartment 64 has been formed in a similar manner.

The length D2 of the plug part, being ca. 0.55 mm, is ca. 20% of the overall length of the linker 63 between the end surfaces 66 and 67.

FIG. 7 shows a typical assembly procedure for a dosage form of FIG. 6. This comprises the following steps:
(1) a first capsule compartment 64 is positioned and supported in a suitable holding means with its mouth opening pointing upwards, and the capsule compartment 64 is filled with a suitable quantity of a drug substance.
(2) a first plug part 69 of a linker 63 is inserted into the open end of the first capsule compartment 64. In this manner the linker 63 forms a closure for the mouth opening of the capsule compartment 64.
(3) a downwardly pointing ultrasonic horn (not shown) is applied to the surface 66 of the linker 63, i.e. to the opposite surface to that of the first plug part 69, and an ultrasonic weld between the linker 63 and the first capsule compartment 64 is formed.
(4) the formed assembly of first capsule compartment 64 and linker 63 is inverted so that the plug part 68 is pointing downwards.
(5) a second capsule compartment 62 is positioned and supported in a suitable holding means (not shown) with its mouth opening pointing upwards, in a manner analogous to step 1, and the second compartment 62 is filled with a suitable quantity of drug substance.
(6) The opposite, second, plug part 68 of the linker 63 is inserted into the open end of the second capsule compartment 62

(7) an ultrasonic horn (not shown) is applied to the outer surface of the second compartment 62 from underneath. An ultrasonic weld is formed between the linker 63 and the second capsule compartment 62.

In an alternative welding mode shown (8) an ultrasonic horn (not shown) is applied laterally as shown by the arrow to the side of the region of contact between the capsule compartment 64 and the linker 63.

In other alternative modes (not shown) thermal, laser or adhesive welds may be formed between the capsule compartments 62 and 64 and the linker 63.

Each of the compartments and sub-units in FIGS. 1 to 6 may be made of the same or different polymer and may have the same or different drug release characteristics. The intermediate capsule compartments are more suitable for a modified release compartment, as dissolution or disruption of the end compartments before the intermediate compartments can occur without disturbance of these intermediate compartments.

The solid sub-units are more suitable as a sustained release sub-unit, as the dissolution of the matrix polymer is likely to occur more slowly than the disruption of the thin wall of a capsule compartment. The hollow bore of unit 313 gives the solid unit 313 a dissolution rate tending toward first-order dissolution kinetics.

Each of the sub-units 12, 13, 14, 22, 23, 24, 32, 33, 34, 35 may contain the same or different drug substance and/or formulation. This may for example be in the form of powder, granulates, or other solid forms. Alternatively the capsule compartments 12, 14, 22, 34 may contain liquid, gel etc. formulations (not shown). The end sub-unit 35 may contain a drug substance or alternately may simply comprise a solid polymer cap devoid of drug substance.

The invention claimed is:

1. A multi-component dosage form comprising:
a plurality of sub-units disposed in end-to-end relationship, each of the plurality of sub-units selected from a group comprising (i) capsule compartment sub-units respectively comprising at least one cavity formed therein and being configured to release a drug-substance contained within the at least one cavity into a gastro-intestinal environment and (ii) solid sub-units comprising a matrix of a polymer;
a first joint formed between a first sub-unit of the plurality of sub-units and a second sub-unit of the plurality of sub-units, the first joint comprising a plug formed as a unitary part of the first sub-unit and a socket formed as a unitary part of the second sub-unit; and
a second joint formed between the first sub-unit and a third sub-unit of the plurality of sub-units, the second joint comprising a socket formed as a unitary part of the first sub-unit and a plug formed as a unitary part of the third sub-unit;
wherein at least one of the first joint and the second joint between respective sub-units is formed such that a relative axial position between respective sub-units is solely delimited by engaging outer wall axial end parts of the respective sub-units;
wherein the first sub-unit is a capsule compartment sub-unit comprising a first cavity including an open end and a closed end and the third sub-unit is a capsule compartment sub-unit comprising a second cavity including an open end and a closed end; and
wherein the open end of the first cavity of the first sub-unit is disposed adjacent the open end of the second cavity of the third sub-unit and the first and second cavities form a combined cavity configured to contain a drug-substance therein.

2. The multi-component dosage form according to claim 1, wherein the plug formed as a unitary part of the first sub-unit is disposed adjacent a first axial end of the first sub-unit and the first sub-unit further includes a socket formed as a unitary part of the first-sub-unit disposed adjacent a second axial end of the first sub-unit.

3. The multi-component dosage form according to claim 1, wherein the second sub-unit is a solid sub-unit comprising a matrix of a polymer.

4. The multi-component dosage form according to claim 1, further including a third joint formed between the second sub-unit and a fourth sub-unit of the plurality of sub-units, the third joint comprising a socket formed as a unitary part of the fourth sub-unit and a plug formed as a unitary part of the second sub-unit.

5. The multi-component dosage form according to claim 4, wherein the fourth sub-unit is a capsule compartment sub-unit comprising at least one cavity formed therein and containing a first drug-substance.

6. The multi-component dosage form according to claim 5, wherein the first sub-unit contains a second drug-substance.

7. The multi-component dosage form according to claim 6, wherein the first drug-substance differs in composition and/or release characteristics from the second drug-substance.

8. The multi-component dosage form according to claim 4, wherein the second and fourth sub-units are capsule compartment sub-units respectively comprising at least one cavity formed therein and containing a drug-substance.

9. The multi-component dosage form according to claim 4, wherein the second sub-unit is a solid sub-unit comprising a matrix of a polymer and the fourth sub-unit is a capsule compartment sub-unit comprising at least one cavity formed therein and containing a drug-substance.

10. The multi-component dosage form according to claim 4, wherein the fourth sub-unit is a solid sub-unit comprising a matrix of a polymer.

11. The multi-component dosage form according to claim 10, wherein the second sub-unit is a capsule compartment sub-unit comprising a cavity formed therein and containing a drug-substance.

12. The multi-component dosage form according to claim 3, wherein the second sub-unit comprises a through-hole formed therein extending from a first axial end of the second sub-unit to a second axial end of the second sub-unit.

13. A multi-component dosage form comprising:
a plurality of sub-units disposed in end-to-end relationship, each of the plurality of sub-units selected from a group comprising (i) capsule compartment sub-units respectively comprising at least one cavity formed therein and being configured to release a drug-substance contained within the at least one cavity into a gastro-intestinal environment and (ii) solid sub-units comprising a matrix of a polymer;
a first joint formed between a first sub-unit of the plurality of sub-units and a second sub-unit of the plurality of sub-units, the first joint comprising a plug formed as a unitary part of the first sub-unit and a socket formed as a unitary part of the second sub-unit; and
a second joint formed between the first sub-unit and a third sub-unit of the plurality of sub-units, the second joint comprising a socket formed as a unitary part of the first sub-unit and a plug formed as a unitary part of the third sub-unit;

wherein the plug formed as a unitary part of the first sub-unit is disposed adjacent a first axial end of the first sub-unit and the socket formed as a unitary part of the first sub-unit is disposed adjacent a second axial end of the first sub-unit;

wherein the first sub-unit is a capsule compartment sub-unit comprising a first cavity including an open end and a closed end and the third sub-unit is a capsule compartment sub-unit comprising a second cavity including an open end and a closed end; and wherein the open end of the first cavity of the first sub-unit is disposed adjacent the open end of the second cavity of the third sub-unit and the first and second cavities form a combined cavity configured to contain a drug-substance therein.

14. The multi-component dosage form according to claim 13, wherein at least one of the first joint and the second joint between respective sub-units is formed such that a relative axial position between respective sub-units is solely delimited by engaging outer wall axial end parts of the respective sub-units.

\* \* \* \* \*